(12) United States Patent
Hames et al.

(10) Patent No.: US 6,737,258 B2
(45) Date of Patent: May 18, 2004

(54) PROCESS FOR THE CONVERSION OF AND AQUEOUS BIOMASS HYDROLYZATE INTO FUELS OR CHEMICALS BY THE SELECTIVE REMOVAL OF FERMENTATION INHIBITORS

(75) Inventors: Bonnie R. Hames, Westminster, CO (US); Amie D. Sluiter, Arvada, CO (US); Tammy K. Hayward, Broomfield, CO (US); Nicholas J. Nagle, Broomfield, CO (US)

(73) Assignee: Midwest Research Institute, Kansas City, MO (US)

( * ) Notice: Subject to any disclaimer, the term of this patent is extended or adjusted under 35 U.S.C. 154(b) by 190 days.

(21) Appl. No.: 10/031,216

(22) PCT Filed: Apr. 10, 2001

(86) PCT No.: PCT/US01/11825
§ 371 (c)(1),
(2), (4) Date: Jan. 11, 2002

(87) PCT Pub. No.: WO01/77296
PCT Pub. Date: Oct. 18, 2001

(65) Prior Publication Data
US 2002/0177199 A1 Nov. 28, 2002

Related U.S. Application Data
(60) Provisional application No. 60/195,416, filed on Apr. 10, 2000.

(51) Int. Cl.$^7$ ............................. C12P 7/06; C12N 1/14; C12N 1/16; C12N 1/18; C12N 1/19
(52) U.S. Cl. ...................... 435/161; 435/162; 435/163; 435/165; 435/252.1; 435/252.9; 435/253.6; 435/255.1; 435/255.2; 435/255.21
(58) Field of Search ................................ 435/161, 162, 435/163, 165, 252.1, 252.9, 253.6, 255.1, 255.2, 255.21

(56) References Cited

U.S. PATENT DOCUMENTS
3,998,732 A   12/1976  Solbach et al.
6,071,729 A  *  6/2000  Jeffries et al. .............. 435/163

OTHER PUBLICATIONS

Perego, P. et al., "Acid hemicellulose hydrolysate: Physical treatments and continuous immobilized–cell fermentations," Bioprocess Engineering, 10: No, 1, 35–41 (1994).

Parajo, J.C. et al., "Improved xylitol production with debaryomyces Hansenii Y–7426 from raw or detoxified wood hydrolysates," Enzyme and Microbial Technology, 21: No. 1, 18–24 (1997).

Machdo, A.E.H., "Photocatalytic degradatio of lignin and lignin models, using titanium dioxide: The role of the hydroxyl radical," Pergamon Press, Oxford, GB, 40: No. 1 115–124 (2000).

Leonard, R.H. and Hajny, G.J., "Fermentation of Wood Sugars," Industrial and Engineering Chemistry, vol. 37, No. 4, 390–395 (1945).

* cited by examiner

Primary Examiner—Jon P. Weber
Assistant Examiner—Kailash C. Snvastava
(74) Attorney, Agent, or Firm—Paul J. White

(57) ABSTRACT

A process of making a fuel or chemical from a biomass hydrolyzate is provided which comprises the steps of providing a biomass hydrolyzate, adjusting the pH of the hydrolyzate, contacting a metal oxide having an affinity for guaiacyl or syringyl functional groups, or both and the hydrolyzate for a time sufficient to form an adsorption complex; removing the complex wherein a sugar fraction is provided, and converting the sugar fraction to fuels or chemicals using a microorganism.

5 Claims, 2 Drawing Sheets

PROCESS FOR THE CONVERSION OF AND AQUEOUS BIOMASS HYDROLYZATE INTO FUELS OR CHEMICALS BY THE SELECTIVE REMOVAL OF FERMENTATION INHIBITORS

The present application claims priority to U.S. provisional application No. 60/195,416 filed Apr. 10, 2000, and to PCT/US01/11825, filed Apr. 10, 2001.

CONTRACTUAL ORIGIN OF THE INVENTION

The United States Government has rights in this invention pursuant to Contract No. DE-AC36-99GO10337 between the United States Department of Energy and the Midwest Research Institute.

TECHNICAL FIELD

This invention relates to industrial fuels and chemicals, and in particular to an improved process for the removal of lignin-derived phenolic compounds from dissolved sugars in an aqueous biomass hydrolyzate and the biological conversion of the sugars into fuels and chemicals.

BACKGROUND ART

As is well known in the biological conversion art, the traditional method for detoxifying a biomass hydrolyzate liquor is overliming. Overliming has been widely used since the 1940's. Leonard, R. H. and Hajny, G. J. Fermentation of Wood Sugars to Ethyl Alcohol, *Industrial and Engineering Chemistry*, vol.37, No. 4, p.p. 390–395 (1945). The basic steps in the overliming process include: adjusting the pH of the hydrolyzate to 10.0±0.1 using $Ca(OH)_2$ or lime, heating the hydrolyzate to 60° C. for 30 minutes, filtering the heated hydrolyzate to remove precipitated solids, and acidifying the filtrate to a pH optimum, which is efficient for the bioconversion of the dissolved sugars into the desired product(s).

A distinct disadvantage of the overliming process is the difficulty in controlling the pH adjustment step. Where a fermentable substrate is a dissolved sugar, strict control over the pH adjustment step is critical because, at a pH greater than 10 one experiences a degradation in the fermentable carbohydrate fraction. It is a further disadvantage in that the mechanism of overliming is not well understood, thereby making it difficult to optimize the process. Moreover, overliming does not detoxify hydrolysis liquors to the extent that an undiluted hydrolyzate comprises an efficient fermentable substrate (overliming allows fermentation at 30%–50% liquor concentration). It is also desirable, in some overliming applications, to use less lime, thereby resulting in the production of less insoluble gypsum, which has been found to precipitate in process lines.

DISCLOSURE OF THE INVENTION

Therefore, it is an object of the invention to provide a process for converting a biomass hydrolyzate into fuels or chemicals using a microbial culture.

It is a further object of the invention to provide a process for detoxifying a biomass hydrolyzate for use as a conversion substrate.

It is still a further object of the invention to provide a process of converting a hydrolysis liquor without first diluting the liquor as a component of the medium.

It is yet another object of the invention to improve the product yield in a microbial chemostat process for converting a biomass hydrolyzate into fuels and chemicals, such as ethanol or lactic acid.

Briefly, the invention provides a process of making a fuel or chemical from a biomass hydrolyzate comprising the steps of providing a biomass hydrolyzate, adjusting pH of the hydrolyzate, contacting a metal oxide having an affinity for guaiacyl or syringyl functional groups or both, and the hydrolyzate for a time sufficient to form an adsorption complex; removing the complex wherein a fermentable sugar fraction is provided, and converting the sugar fraction into a fuel or chemical using a microorganism.

The foregoing specific objects and advantages of the invention are illustrative of those which can be achieved by the present invention and are not intended to be exhaustive or limiting of the possible advantages which can be realized. Thus, those and other objects and advantages of the invention will be apparent from the description herein or can be learned from practicing the invention, both as embodied herein or as modified in view of any variations which may be apparent to those skilled in the art.

BRIEF DESCRIPTION OF THE DRAWINGS

The accompanying drawings, which are incorporated in and which constitute a part of the specification, illustrate at least one embodiment of the invention and, together with the description, explains the principles of the invention.

DESCRIPTION OF PREFERRED EMBODIMENTS

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

As used herein the term "phenolic" is an adjective meaning a member of the class of phenols. "Phenols" means the class of aromatic compounds in which one or more hydroxyl groups are attached directly to a benzene ring. Examples of phenols include phenol, cresol and resorcinol. "Biomass or lignin-derived phenols" include the compounds known as guaiacol, syringol, isoeugenol and vanillin.

A microbial process of converting a biomass hydrolyzate, such as wood, into fuels and chemicals is described. The process uses adsorption of the biomass hydrolyzate on a solid metal oxide support, such as titanium dioxide, for the selective removal of substances, such as lignin-derived compounds, which inhibit product formation in a traditional chemostat culture. The adsorption step is highly selective, to provide an efficient method for the fractionation of the hydrolyzate, 90% of the hydrolyzate's dissolved lignin-derived compounds being removed without a measurable decrease in the hydrolyzate's dissolved sugar concentration. Dissolved sugars and lignin-derived phenolic compounds are thereby fractionated into a fermentable medium for use in a traditional microbial chemostat process for making fuel and chemical products. The invention improves the product yield over the prior art methods for making fuels and chemicals from an undiluted biomass substrate.

Figure 1:
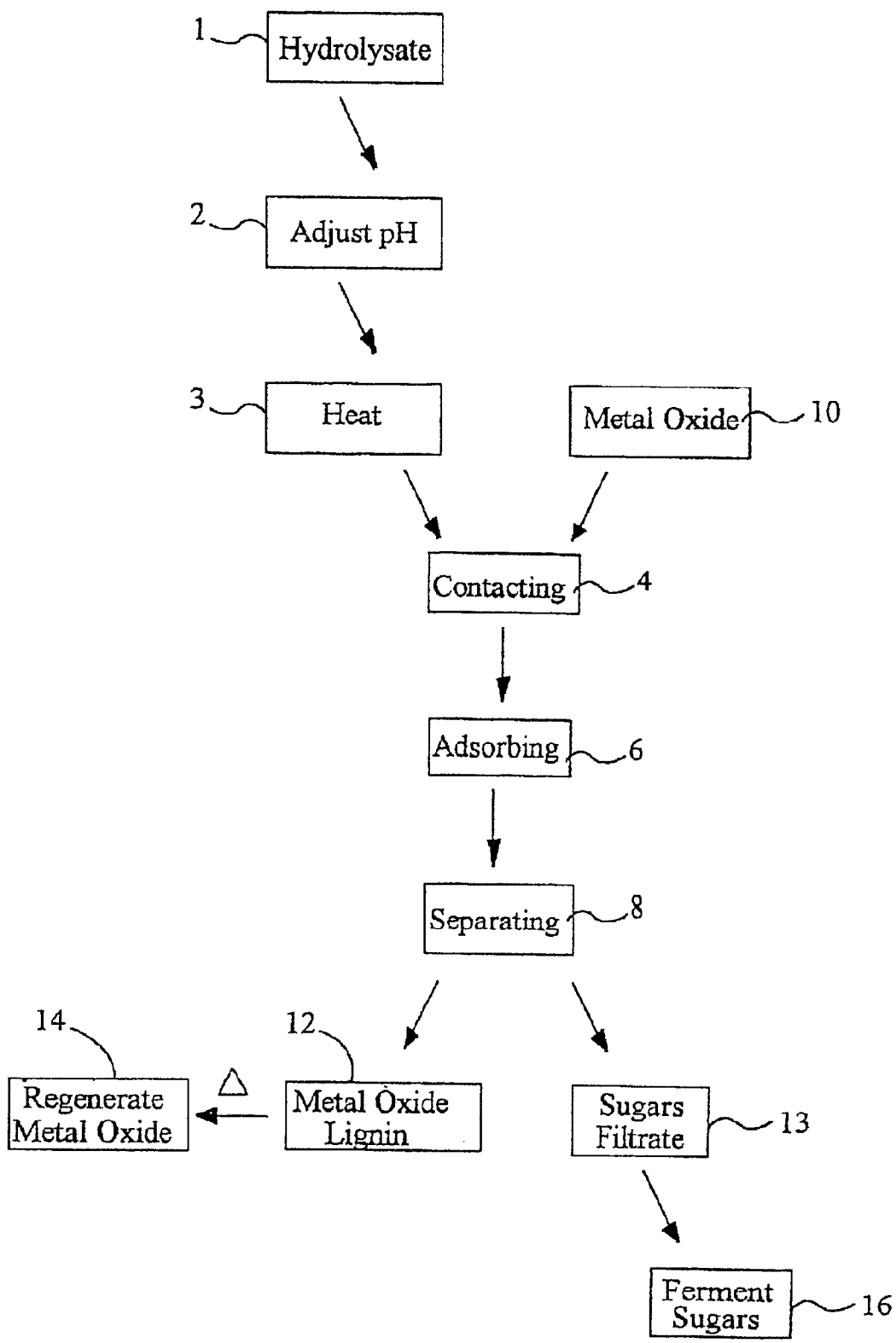
FIG. 1 is a flow chart of an embodiment of the process.

With reference now to the drawing figures, FIG. 1 is a flow chart of a preferred embodiment of the process according to the invention herein. In FIG. 1, a biomass hydrolyzate liquor 1 is preferably obtained from a sulfuric acid hydrolyzed soft or hardwood. The pH of hydrolyzate is about 2.0. The hydrolyzate liquor 1 is adjusted to a pH within the range of 6–10, preferably 8.0–9.2, using Ca(OH)$_2$. The removal of reactants from the hydrolysis liquor 1 which inhibit product formation increases with an upward adjustment in pH to 10, which is the pH where the fermentable carbohydrate fraction begins to degrade.

After the adjust pH or adjusting 2 step of the pH of the hydrolyzate liquor 1 it, may but need not, be heated 3 to a temperature in the range of 60° C.–90° C., preferably 90° C., and the heated hydrolysis liquor is mixed in suspension for contacting with a metal oxide 10, such as a Norton Chemical Process Products Company, Akron, Ohio, high-surface-area TiO$_2$ ⅛" extrudate, type XT 25384, or anatase TiO$_2$, Aldrich Chemical Company. The suspension is allowed to cool at room temperature. High separation efficiency is generally achieved by using an amount (wt/wt) of TiO$_2$ 10 which is twice the estimated phenol concentration of the hydrolysis liquor 1. This ratio varies, however, with the form, source, active surface area and liquid-contact surface area of the TiO$_2$ to be used. For example, where a softwood is the starting material for the hydrolyzate, absorption requires a 4:1 oxide to lignin-derived compounds weight ratio in order to sufficiently remove those substances from the liquor which inhibit product formation. Separation efficiency also varies with the age of the aqueous mixture and the source of the biomass hydrolyzate 1. Producing hydrolyzate under conditions of high severity will also reduce the separation efficiency for removing inhibitory reactants.

Selective adsorbing step 6 is accomplished using all grades of TiO$_2$. Rate and adsorption efficiency of TiO$_2$ for aromatic compounds depends on the area of active TiO$_2$ surface area. Anatase titanium dioxide is preferred over the rutile form, and may comprise any high-surface-area formulation, such as powders, thin-films, sol-gel crystals, or extruded pellets. Vanadium and zirconium oxides and, when processing at a pH in a range of greater than 7.0, manganese dioxide, silica, and alumina, may also be used as an adsorbent.

A batch reaction vessel or plug-flow reactor may be used as an adsorption vessel, depending upon the quantity of the aromatic compounds to be separated from the hydrolyzate prior to the fermentation step. In the batch reactor a retention time of 30 min. is preferred. In a plug-flow reactor the preferred retention time is 15 minutes. Adsorption retention for these lengths of time typically results in a removal of up to 90 weight percent (wt %) of the aromatic compounds from the hydrolyzate 1 that inhibit product formation. Longer retention times are desirable where the adsorption step 6 is processed at a low pH. The adsorption is slow in the pH range of 2–6 and more rapid when the pH is in the range of 7–10.

The adsorbing step 6 retains its efficiency and selectivity throughout a temperature in the range of 20° C.–90° C. Also conditions of elevated temperature and pH do not affect adsorption selectivity relative to the soluble carbohydrate fraction. However, above pH 6 some carbohydrate degradation products, such as 5-(hydroxymethyl)furfural (HMF) and furfural, are adsorbed on the metal oxide 10 surface. Furthermore, under basic conditions at high temperature some entrainment of soluble salts occurs on the metal oxide surface when the mixture includes a salt, having low solubility at high temperature, such as calcium sulfate. Increasing both the temperature and pH does not affect adsorption selectivity for lignin-derived compounds.

After contacting 4 the hydrolyzate 1 and metal oxide 2 adsorption preferably includes agitating the suspension for a time sufficient to allow colloidal particles to deposit on the TiO$_2$ surface. A clearing of the suspension when it is allowed to settle at room temperature for 1 hour is indicative of the adsorbed complex having been formed. The adsorbed complex is then separated in separation step 8, such as with a glass-fiber filter. The resulting sugars filtrate 13 thereby includes the fermentable carbohydrate fraction useful for conversion into fuels or chemicals. The filtrate 13, of the fractionated hydrolyzate liquor, may be used as an undiluted carbohydrate source for conversion into fuels and chemicals, by any well known microbial process, including ethanol or lactic acid.

Figure 2:
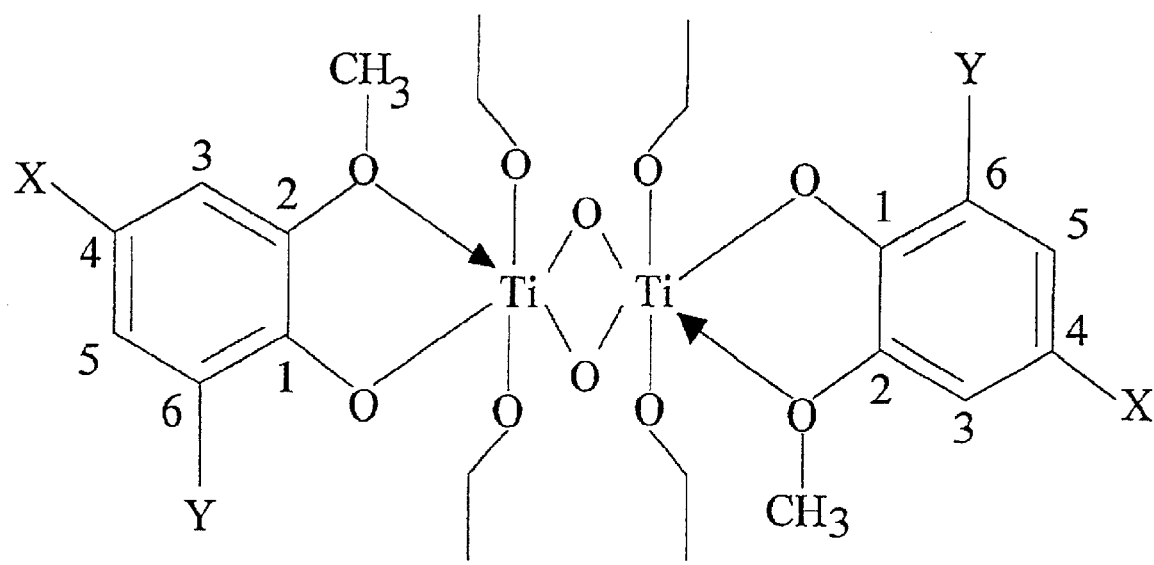
FIG. 2 is a graphical illustration that demonstrates the affinity for oxygen molecules adjacent to the lignin aromatic ring for a titanium dioxide surface.

Referring now to FIG. 2, one unique aspect of the adsorption step 6 is its high separation selectivity of the metal oxide for lignin-derived compounds present in an aqueous hydrolysis liquor having an excess of monomer fermentable sugars. Greater than 90% of the soluble lignin component is removed from the hydrolyzate without any loss of glucose or xylose. When using TiO$_2$ extruded pellets as an adsorbent, a slight concentration effect is observed during the adsorption process. This effect may be due to hydration of the metal oxide and the exclusion of sugars from the metal oxide's surface. Solid state nuclear magnetic resonance (nmr) analysis of lignin-derived model compounds, adsorbed on a TiO$_2$ surface, shows that lignin-derived selectivity is due, at least in part, to the affinity of titanium for adjacent oxygen molecules which are located on the aromatic ring structure of the adsorbed substrates. See FIG. 2, Guaiacol: X=Y=H; Isoeugenol: X=CH$_3$CH=CH—, Y=H; Syringol: X=H, Y=OMe. Through chemical shifts in $^{13}$C nmr between lignin model compounds, both before and after formation of the complex with titanium alkoxides, it has been found that these molecules bind preferentially through the phenol oxygen and the oxygen of the adjacent methoxyl group. The biomass-derived aromatic substituents have two main substitution patterns, commonly known as guaiacyl and syringyl, which contain the functional groups necessary for selective fractionation. Although titanium, and many other transition metals, is known to be highly oxyphilic the affinity of this functionality for these metal oxides is so strong that in the presence of these aromatic compounds even highly oxygenated carbohydrate-derived compounds are excluded from the metal oxide surface.

The process may, but need not, include a regeneration step 14. In this step, metal oxide adsorbents are regenerated using combustion of the adsorbed complex or metal oxide lignin 12 for 15 minutes at 400° C. An estimated 100 to 500 regeneration cycles may be utilized without a significant reduction in lignin-derived compound selectivity. Regeneration 14 of TiO$_2$ at a temperature of less than 600° C. avoids an anatase to rutile form conversion, which decreases the metal oxide's capacity for adsorption. A simple regeneration wash step using dilute sulfuric acid may also be used to increase the lifetime of TiO$_2$ adsorbents when the contacting step 4 is carried out at a pH greater than 7. When manganese dioxide is used, the adsorbent regeneration 14 has also been demonstrated for 15 minutes at 575° C.

EXAMPLE 1

This example demonstrates the resulting lignin-derived compound and glucose concentrations after adsorption of a biomass hydrolyzate using three different sets of process variables. Sample No. 1 was prepared using a 50 mL aliquot of a well mixed hydrolysis liquor, containing a large amount of suspended solids, and 10 grams of Norton high-surface-area TiO$_2$, in a 100 mL beaker. The sample was agitated by hand for approximately 5 minutes until the mixture became clear (colloidal particulates deposited on the surface of the TiO$_2$). The mixture was allowed to settle at room temperature for 1 hour and filtered through a glass filter, Watman GFC, the filtrate being stored in a glass container.

Samples Nos. 2 and 3 were prepared by mixing a 50 mL aliquot of a well-mixed hydrolysis liquor, containing a large amount of suspended solids, in contact with 10 grams of $TiO_2$, high surface area, in a 100 ml beaker. Unlike sample No. 1, the $TiO_2$ in sample No. 2 was left in solution at room temperature without stirring for 8 hours (sample No. 2) prior to the separation of the $TiO_2$ adsorption complex by gravity filtration. Half of the liquid (approximately 20 ml), of sample No. 2, was decanted and filtered for lignin-derived compound and glucose determination, and the other half was retained in contact with $TiO_2$ overnight (sample No. 3). The beaker was covered with aluminum foil to minimize evaporation. After 20 hours, the remaining liquid of sample No. 3 was decanted from the $TiO_2$ adsorption complex and filtered through a glass Watman GFC filter. Filtrates for each sample were diluted with dilute $H_2SO_4$ and analyzed for their phenol concentrations by measuring UV absorbency at 204 nm. In addition, glucose concentrations for the filtrates were measured using a YSI, Yellow Springs Instruments Co., glucose analyzer.

The results of this example are summarized in Table 1. In the table, most of the adsorption occurs within the first hour and very little change is observed in either adsorption or selectivity with prolonged exposure. The absorbency at 204 nm (measured using a UV/visible spectrophotometer) reflects the concentration of the phenolic compounds remaining in the treated liquor. The absorbency at 282 nm reflects the concentration of furfural and 5-(hydroxymethyl) furfural.

TABLE 1

| Sample | Absorbance 204 nm | Absorbance 282 nm | Lignin mg/mL | Glucose mg/mL |
|---|---|---|---|---|
| Original Liquor | 1.0763 | 0.591308 | 6.3 | 9.4 |
| Sample No. 1 (1 h) | 2.14941 | 0.409973 | 1 | 10.8 |
| Sample No. 2 (8 h) | 1.48932 | 0.448135 | 0.7 | 11 |
| Sample No. 3 (16 h) | 1.29463 | 0.5885 | 0.6 | 10.3 |

EXAMPLE 2

This example demonstrates the ability of three different microorganisms to convert the carbohydrate fraction of the hydrolyzate into ethanol and lactic acid. An undiluted hydrolysis liquor was prepared at pH 9.0, at 90° C. for 1 hour, with a $TiO_2$ to lignin-derived compound ration of about 4/1. The hydrolysis liquor was either an acid hydrolyzate of a poplar hardwood or a mixture of softwoods. Three microorganisms r. *Zymomonas mobilis, Saccharomyces cerevisae* $D_5A$, and *Lactobacillus rhamnosus* were used to evaluate the conversion efficiency of an undiluted hydrolysis liquor to ethanol and lactic acid. The fermentations were carried out in a chemostat culture, the results of which were measured and reported as the percent product yield of a glucose control. The results of these fermentation's are summarized in Table 2.

TABLE 2

| Liquor Feedstock Concentration (vol./vol.) | Microorganism | Product | Best Yield (% Glucose Control) |
|---|---|---|---|
| Poplar-hardwood (80%) | Zymomonas mobilis | ethanol | 90 |
| QLG mixed softwoods (80%) | Saccharomyces cerevisae | ethanol | 123 |
| QLG mixed softwoods (80%) | Lactobacillus rhamnosus | L(+) Lactic acid | 100 |

A hydrolyzate concentration of 80% (v/v) represents the maximum or full-strength batch-mode fermentation, because the remaining 20% is a 10% (v/v) inoculum and a 10X strength nutrient media. A 30% liquor concentration means that the fermentation has 30% (v/v) hydrolyzate, 20% inoculation media, 2% supplemental sugars and the balance is water.

The detoxification of various hydrolysis liquors is demonstrated in Table 2. Results are shown for the fermentation of both hardwood and softwood liquors. Two different organisms, r. *Z. mobilis* and *S. cerevisae*$D_5A$ were used for the fermentation of the detoxified liquors to produce ethanol. The third table entry shows that, for the process of the invention, detoxification also enhances the biological conversion of hydrolyzed sugars to lactic acid using an *L. rhaminosus* organism. The performance of the yeast *S. cerevisae* $D_5A$, in converting sugars in the softwood liquor to ethanol was better than the pure sugar control. The enhanced fermentation of the hydrolysis liquor may be due to the buffering effect of other hydrolysis liquor components and a slightly higher initial sugar level in the hydrolysis test sample.

While the present invention has been illustrated and described with reference to particular structures and methods of fabrication, it will be apparent that other changes and modifications can be made therein with the scope of the present invention as defined by the appended claims.

What is claimed is:

1. A process of making a fuel or chemical from a biomass hydrolyzate comprising:

(a) providing a biomass hydrolyzate;

(b) Adjusting the pH of said biomass hydrolyzate within a range of 6–10.0;

(c) contacting a metal oxide selected from the group consisting of titanium dioxide, vanadium oxide, and zirconium oxide having an affinity for guaiacyl or syringyl functional groups or both with said biomass hydrolyzate for a time sufficient to form an adsorption complex comprising a compound consisting essentially of phenol compounds obtained from lignin and a dissolved sugar fraction; wherein the amount of metal oxide is 2:1 to 4:1 of the weight ratio of said phenol compounds obtained from lignin;

(d) removing the adsorption complex; and (e) converting the dissolved sugar fraction into a fuel or chemical using a microorganism selected from the group consisting of r. *Zymomonas mobilils, Saccharomyces cerevisae* $D_5A$, or *Lactobacillus rhamnosus*.

2. The process of claim 1 further comprising, after adjusting the pH, heating the biomass hydrolyzate to a temperature in the range of 80° C. to 100° C.

3. The process of claim 1 wherein the metal oxide is titanium dioxide, and said titanium dioxide is 2:1 of the weight ratio of said phenol compounds of the biomass hydrolyzate.

4. The process of claim 1 wherein said biomass hydrolyzate is from a softwood.

5. The process of claim 1 wherein the dissolved sugar fraction includes less than one mg/mL of phenol compounds obtained from lignin.

* * * * *